United States Patent [19]

Tsuda et al.

[11] Patent Number: 5,089,483
[45] Date of Patent: Feb. 18, 1992

[54] AGENT FOR PRESERVATION OF TIMBER AGAINST DECAY AND TERMITE DAMAGE

[75] Inventors: Kenji Tsuda, Himeji; Shoichi Ono, Odawara, both of Japan

[73] Assignees: Daicel Chemical Industries Ltd., Sakai; Shokusan Jutaku Sogo Co., Ltd., Tokyo, both of Japan; a part interest

[21] Appl. No.: 468,128

[22] Filed: Jan. 22, 1990

[51] Int. Cl.$^5$ .................. A01N 55/08; A01N 59/14
[52] U.S. Cl. ..................................... 514/64; 424/660; 424/DIG. 11
[58] Field of Search .................. 514/64, 663; 424/660, 424/DIG. 11

[56] References Cited

FOREIGN PATENT DOCUMENTS 63-101306  5/1988  Japan .
1098733  1/1968  United Kingdom .

OTHER PUBLICATIONS

Chemical Abstracts (68: 77712v), 1968.
Chemical Abstracts (109: 224732x), 1988.
Chemical Abstracts (111: 133241m), 1989.

Primary Examiner—Frederick E. Waddell
Assistant Examiner—K. Weddington
Attorney, Agent, or Firm—Fleit, Jacobson, Cohn, Price, Holman & Stern

[57] ABSTRACT

The antidecay and antitermite agent for timber of the invention contains alkyldimethylamine tetraborate as an effective component; the compound can be applied as it is or in a form of preparation to the sites where termites are generated, termitoria, construction members such as pillars, buildings and soils surrounding the buildings, waterproof sheets, paving materials and covering materials for wires or cables or the like by such means as painting, blowing, soaking, injecting, spraying, mixing and kneading.

1 Claim, No Drawings

AGENT FOR PRESERVATION OF TIMBER AGAINST DECAY AND TERMITE DAMAGE

BACKGROUND OF THE INVENTION

The present invention relates to an antidecay and antitermite controlling agent for timber, which can preserve timber against decay and at the same time prevent and control termite damage to the timber.

The need of agents for the preservation of timber against decay and those for the prevention and control of termite damage to timber has become pressing with the diversification of timber utilization as well as the change in life style in recent years. For example, under environmental conditions of housing today, timbers used for foundations or the like are deteriorated in a short period of time by wood-rotting fungi represented by *Tyromyces palustris, Merulius lacrymans* and *Coriolus versicolor*. Furthermore, the termite damage to housings and trees has been kent increasing for these years; the estimated damage in Japan reaches as much as tens of millions of yen annually. The damage is frequently found in places with high humidity, such as under the floor, and in a kitchen, a bathroom and a lavatory. On the other hand, in such places where the humidity is high, timbers are easily decayed, which in turn makes in turn the timbers susceptible to the damage by termites. Therefore, preservation of timber against decay is effective also in terms of controlling damage by termites; thus antidecay agents and antitermite agents are indispensable as agents for the preservation of timber.

Known examples of agents conventionally used for preservation of timber against decay include organic agents, e.g. phenol compounds, organic halogen compounds, organic tin compounds, naphthenic acid compounds and tar compounds, and inorganic compounds, e.g. Walman salt compounds (a mixture of fluoride compounds, chromic compounds and phenols).

However, the conventional organic agents have disadvantages such that they are strongly toxic to humans and animals and cause irritation and rashes on the skin, and furthermore they have unpleasant order and stain timbers. On the other hand, the inorganic agents have to be used at high concentrations, so that large amounts are needed. Furthermore, some conventional termite-controlling agents exert adverse effects on human and animals; for example, CCA agents contain harmful metals or organic chloride compounds and organic phosphate compounds are strongly toxic.

SUMMARY OF THE INVENTION

An object of the present invention is therefore to provide an antidecay and antitermite agent for the reservation of timber, which is less toxic and has both antidecay and antitermite effects.

In order to achieve the above-mentioned object, the present inventor has studied in many respects on boric acid and compounds thereof which are said to have a termite controlling activity but not an antidecay activity, and thus found that not a metaborate but tetraborate of the above-mentioned amine is obtained when alkyldimethyl amine reacts with metaboric acid and that the obtained substance has not only the activity for controlling termite damage but also the antidecay activity, thereby completed the present invention.

DETAILED DESCRIPTION OF THE INVENTION

The antidecay and antitermite agent for timber according to the present invention contains alkyldimethylamine tetraborate represented by the following general formula or the hydrate thereof as an effective component.

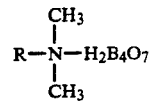

in the formula, R represents an alkyl group having 8 to 20 carbon atoms. The agent containing this alkyldimethyl tetraborate or the hydrate thereof possesses not only an inhibitory effect on the growth of wood-rotting fungi such as *Tyromyces palustris* and *Merulius lacrymans* but also an insecticide activity to termites such as *Reticulitermes speratus*.

Examples of alkyldimethylamine comprising the compound of the present invention include octyldimethylamine, decyldimethylamine, lauryldimethylamine, tetradecyldimethylamine, cetyldimethylamine and octadecyldimethylamine.

The compound of the present invention can be obtained by reacting the above-mentioned amine with metaboric acid, orthoboric acid or tetraboric acid or the mixture thereof at 140° to 170° C. From a viewpoint of the reactivity, metaboric acid or orthoboric acid, particularly metaboric acid, is preferably used.

The compound of the present invention can be used as it is but may generally be used in a form of emulsion with water or as an oil agent by dissolving in an appropriate organic solvent. Alternately, it can be used as a mixture with a water emulsion and a solvent-type paint.

The concentration of the effective component in an agent containing the compound of the present invention and the amount of the dose of the agent may be arbitrarily selected depending on the method and the object of the application, i.e. whether the treatment is on timber or on soil.

However, the ratio of the effective component, alkyldimethylamine tetraborate, to be practically used is 0.1 to 20% by weight, and 1 to 10% by weight is particularly effective.

The compound per se or the preparation thereof, according to the present invention, can be applied to the sites where termites are generated or territoria or the materials on which the termite damage has to be prevented, such as construction members, e.g. foundations and poles, buildings and surrounding soils thereof, waterproof sheets, paving members and coating materials for wires or cables, by painting, blowing, soaking, injecting, spraying, mixing, kneading or by other means.

The compound of the above-mentioned composition can control growth of wooden-rotting fungi such as *Tyromyces palustris, Merulius lacrymans* and *Coriolus versicolor* and at the same time exerts an insecticidal effect on termites.

The present invention will be explained in more detail, referring to an example of preparation and tests for antidecay and antitermite activity hereinbelow.

A. EXAMPLE OF PREPARATION

Lauryldimethylamine (21.3 grams, 0.1 mole) and metaboric acid (4.4 grams, 0.1 mole) were placed in a three-opening flask equipped with an evaporating device and a stirrer and heated at 140° to 150° C. for 1 hour with stirring. About 20 minutes after the onset of the reaction, the reacting content turns to be a nearly transparent, viscous solution. Water produced during the reaction was removed outside the reaction system passing through the evaporating device. After completion of the reaction, the reaction content was cooled down to room temperature, stirred with an addition of 200 ml of hexane to extract unreacted amine and then filtered. Insoluble cakes were crushed in a mortar in a powder form; 200 ml of hexane was added again and filtration was repeated 2 times after stirring at about 50° C. for 1 hour. The resulting residue was dried in air for 1 day and then at 60° C. for 2 hours in vacuo to obtain lauryldimethylamine tetraborate. Solubility of the above-mentioned compound in various solvents at 20° C. is shown in Table 2.

TABLE 1

| Solvent | Reaction product in Example 1 Concentration (%) | | |
|---|---|---|---|
| | 1 | 5 | 10 |
| Water | Δ | x | x |
| Alcohol | ○ | ○ | ○ |
| Isopropyl alcohol | | | |
| Ketone | | | |
| Acetone | Δ | x | x |
| Methylisobutylketone | x | x | x |
| Aromatic groups | | | |
| Benzene | ○ | x | x |
| Xylene | ○ | x | x |
| Others | | | |
| Hexane | x | x | x |
| Chloroform | ○ | x | x |
| Dimetylsulfoxide | ○ | ○ | x |

In the Table 1, ○ represents very soluble; Δ sparingly soluble; and × insoluble.

B. EXAMPLE OF TEST FOR THE ACTIVITY TO PRESERVE TIMBER AGAINST DECAY (1) Testing Procedure 1) A cellulose sheet, 2 cm×2 cm in size, was soaked in a 5% lauryldimethylamine tetraborate water emulsion for several seconds and dried in air for 24 hours and then at 60°±2° C. for 1 hour.

2) A molt extract agar medium was dispensed in plates and solidified to use as a culture medium.

3) Test fungi were inoculated on the surface of each medium at the four corners; when the fungi sufficiently grow spreading over the medium, the cellulose sheet soaked with the agents was placed near the center of the medium.

(2) Results of the Test

Cultivation was carried out at 26°±2° C. for 1 week, and then the cellulose sheet was examined for the growth of the test fungi.

A cellulose sheet without soaking the agents was treated in the same manner and used as a control.

The results of the test are shown in Table 2.

TABLE 2

| | Test fungi | |
|---|---|---|
| | Tyromyces palustris | Coriolus versicolor |
| Control | Fungal growth | Fungal growth |
| Lauryldimethylamine tetraborate | Entirely no fungal growth | Entirely no fungal growth |

C. EXAMPLE OF TESTING THE ANTITERMITE ACTIVITY IN TIMBER (1) Testing Procedure 1) Timber strips used for the test were sapwood of normal and *Pseudotsuga taxifolia* and *Tsuga diversifolia*, which were cut rectangular and planed smooth on all the sides (approximately 5).

2) Test timber strips were soaked in a 5% lauryldimethylamine tetraborate water emulsion for 1 hour and then dried at 60° C. to reach constant temperature.

3) Soil was placed in a glass container (8 cm in diameter, 6 cm in height) at a depth of about 4 cm. Subsequently, in the container, termites (*Reticulitermes speratus*, 200 workers and 4 soldiers) were placed and then the timber strips (one each of *Pseudotsuga taxifolia* and *Tsuga diversifolia*) soaked with the test sample were horizontally placed one by one. The container was allowed to stand for 21 days to rear the termites.

(2) Results of the Test

Observation was made to examine after rearing for 21 days whether the wood strips were suffered from damage caused by the termites or not. The results are shown in Table 3.

TABLE 3

| Sample | Damage observed |
|---|---|
| Control | Severe damage |
| Lauryldimethylamine tetraborate | Entirely no damage |

As demonstrated above, the compound of the present invention has alkyldimethylamine tetraborate or the hydrate thereof as an effective component, exerts less toxicity to humans and animals thus effectively preserve timber against the decay and termite damage.

What is claimed is:

1. A method of protecting timber from decay and termites, comprising the step of:
applying thereto a protective amount of an compound having the formula alkyldimethylamine tetraborate or hydrate thereof having the formula:

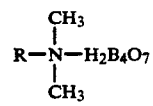

wherein R represents an alkyl group having 8 to 12 carbon atoms.

* * * * *